United States Patent [19]

Rhiner

[11] Patent Number: 5,012,119
[45] Date of Patent: Apr. 30, 1991

[54] METHOD AND APPARATUS FOR MONITORING PARTICLES USING BACK-SCATTERED LIGHT WITHOUT INTERFERENCE BY BUBBLES

[75] Inventor: Walter Rhiner, Cupertino, Calif.
[73] Assignee: Xinix, Inc., Santa Clara, Calif.
[21] Appl. No.: 353,963
[22] Filed: May 19, 1989
[51] Int. Cl.$^5$ .................... G01N 15/07; G01N 21/49
[52] U.S. Cl. ..................................... 250/574; 356/343
[58] Field of Search ................ 250/574, 575; 356/340, 356/341, 342, 343

[56] References Cited

U.S. PATENT DOCUMENTS 4,419,903  12/1983  Jackson ............................ 250/574
4,662,749  5/1987  Hatton et al. .................... 250/574

Primary Examiner—David C. Nelms
Assistant Examiner—William L. Oen
Attorney, Agent, or Firm—William Green & Assoc.

[57] ABSTRACT

A method and apparatus for determining the amount and size of particles and bubbles in a liquid process medium. The invention comprises the steps of providing a collimated light source to generate a light beam of a known wavelength, and directing it to illuminate a liquid sampling volume within a cell positioned within a sensor housing constructed to collect the light scattered by particles and/or bubbles within the sample caused by the impingement of the light beam. The scattered light is then separated into forward, and/or right angle and back scattering portions, and converted into separate electrical signals for each scatter direction. Since the scattering coefficient is a direct function of the density of the sampling volume, the presence of bubbles reduces the density and the amount of radiation scattered in the backward direction. Using the level of scattering resulting from the liquid medium alone as a reference, particles and bubbles within the sampling volume each scatter radiation at a level that results in significant and substantially similar positive signals in the forward and/or right angle scattered channels. As a result bubbles and particles are not distinguishable in the forward or right angle scatter channels. Heretofore it has been known that back scattering exists in sample volumes containing bubbles and particles, however the presence and amount of the back scattering has not been correlated to the presence or absence of bubbles. In this invention it has been found that in contrast to the forward and/or right angle scattering characteristics, the presence of bubbles within the sampling volume results in a significant negative signal in the back scatter channel while on the otherhand the presence of particles within the sampling volume results in only a small positive signal in the back scatter channel. This difference in the scattering characteristics of bubbles and particles permits the separate signals from both forward and/or right angle scattering and back scattering to be processed to determine the size and quantity of particles and/or bubbles relative to the medium being monitored.

8 Claims, 1 Drawing Sheet

A) FORWARD/ RIGHT ANGLE SCATTER SIGNAL
B) BACK SCATTER SIGNAL LEVEL

METHOD AND APPARATUS FOR MONITORING PARTICLES USING BACK-SCATTERED LIGHT WITHOUT INTERFERENCE BY BUBBLES

BACKGROUND OF THE INVENTION

1. Field of the Invention

This invention relates generally to optical methods and apparatus for determining the size and quantity of particles and bubbles in liquid mediums. More specifically it relates to the monitoring and/or analysis, either real-time or off-line, to detect and to distinguish particles and bubbles in process liquids used in manufacturing applications where the purity of a liquid medium is important, such as semiconductor or medical applications.

2. Brief Description of the Prior Art

Particles are generated in the manufacture of semiconductor devices, which contaminate liquids used during wafer fabrication, such as chemical etches, photo resists deionized water and solvents, used during wafer processing, generate particles. The number of defects and thus process yield is known to be directly proportional to the presence and number of particles in the liquid medium used for processing. Modern wafer processing methods require minimizing the amount of particulate matter in all liquids in contact with the wafers. Thus process mediums are monitored for particle contamination and various filtering methods are utilized to remove particles.

Since bubbles generate signals which are indistinguishable from particles in conventional methods for monitoring semiconductor liquids during processing, bubbles are measured and counted as particles.

Particles larger than 1 micron can be successfully filtered, however reliable removal of particles smaller than 1 micron becomes progressively more difficult. As the art of wafer processing advances, purity standards for the processing medium become more stringent and the detection of particles down to 0.1 micron or less is desirable.

No satisfactory in-line method for physically separating bubbles from sub-micron particles for wafer processing has been found.

Because of the difficulty in discriminating between particles and bubbles, prior art devices count both particles and bubbles which are not distinguishable from particles, thus the count is a pseudo particle count rather than a true particle count. Because of this pseudo particle count the process medium is prematurely determined to be exhausted and rejected.

In many applications used process liquid is environmentally harmful and often the appropriate methods for disposal require expensive special handling. The premature rejection of process liquid also increases the cost of processing.

When the particle count exceeds the allowable level, the number of defects increases and the process yield declines.

Particle monitors exist which measure off-line samples of the process medium or which are positioned in the process bath recirculating lines, however due to particle dynamics such monitors, in reality, measure filter efficiency and not on-line bath conditions. Furthermore, such monitors do not distinguish between particles and bubbles.

A requirement of any sampling device which is on-line and in contact with the process medium is that the sampling system not generate or introduce additional particles. The materials which contact the process medium must be non-reactive within the medium.

The principal object of this invention is a method and device for reliably detecting the presence and quantity of sub-micron particles in the presence of bubbles.

Another object of this invention is the detection of particles of down to 0.1 micron or less, within liquid mediums.

It is another object of this invention to more efficiently detect the point at which the particle count has exhausted the effectiveness of the medium, thus eliminating premature rejection and reducing the disposal problems.

It is yet another object of this invention to accurately detect the point at which the quantity of particles causes an unacceptable yield and to signal the process controller to change the medium.

It is still another object of this invention to provide a real-time on-line measurement of particles.

A further object of this invention is to monitor bacteria count in the presence of particles and bubbles.

Yet another object of this invention is to provide a sample handling device and method which is unobtrusive, which does not generate additional particles, which is protected from toxic substances within the bath, and which assures a representative sample.

Hatton and Plawsky in U.S. Pat. No. 4,662,749 Fiber Optic Probe and System for Particle Size and Velocity Measurement, disclose and discuss prior art methods and apparatus for measuring particles. Tatsuno in U.S. Pat. No. 4,595,291 Particle Diameter Measuring Device, discloses the use of laser beams and optical fibers for directing a light source and monitoring light scattered by particles for particle measurement. Philip H. Paul and George Kychakoff in "A Miniature Fiber-Optic Probe for Optical Particle Sizing" Journal of Lightwave Technology Vol. LT-5, No. 7, July, 1987 discuss the use of laser beams and detection of forward and right angle scattered light for measuring particle size.

SUMMARY OF THE INVENTION

The present invention is a method and device for particle detection, sizing, and monitoring in which a light source of a known wavelength is directed to illuminate a sampling volume in a cell positioned within a sensor housing having optical devices constructed to separately collect forward scattered light, right angle scattered light, and back scattered light. The light from each direction is then fed to detectors, such as photo diodes, and converted into individual electrical signals which are proportional to the level of light detected. The electrical signals are then transmitted to an electronic decoder which can detect and process the signals into information, which using the rationale explained below permits the determination of the size and quantity of particles and/or bubbles in the medium being tested.

This invention is based upon the premise that optically, the back scatter levels of bubbles are significantly different from those of particles and particles may be distinguished from bubbles by their markedly different scattering. In addition it is known that scattering coefficients are a direct function of the density of the medium. Thus the amount of back scatter by a liquid medium containing bubbles is reduced in the presence of a bubble. Consequently, the total energy sensed by back scattering detectors with the presence of a bubble in the cell produces a negative pulse when compared to a back scattering reference level. In contrast, particles will produce a small positive signal in the back scattering detector as well as positive signals in the forward and right angle scattering detectors. The analysis of the combination of these signals by conventional signal processing techniques results in increased sensitivity of particle detection and the ability to distinguish between bubbles and particles.

DETAILED DESCRIPTION OF THE INVENTION

Figure 1:
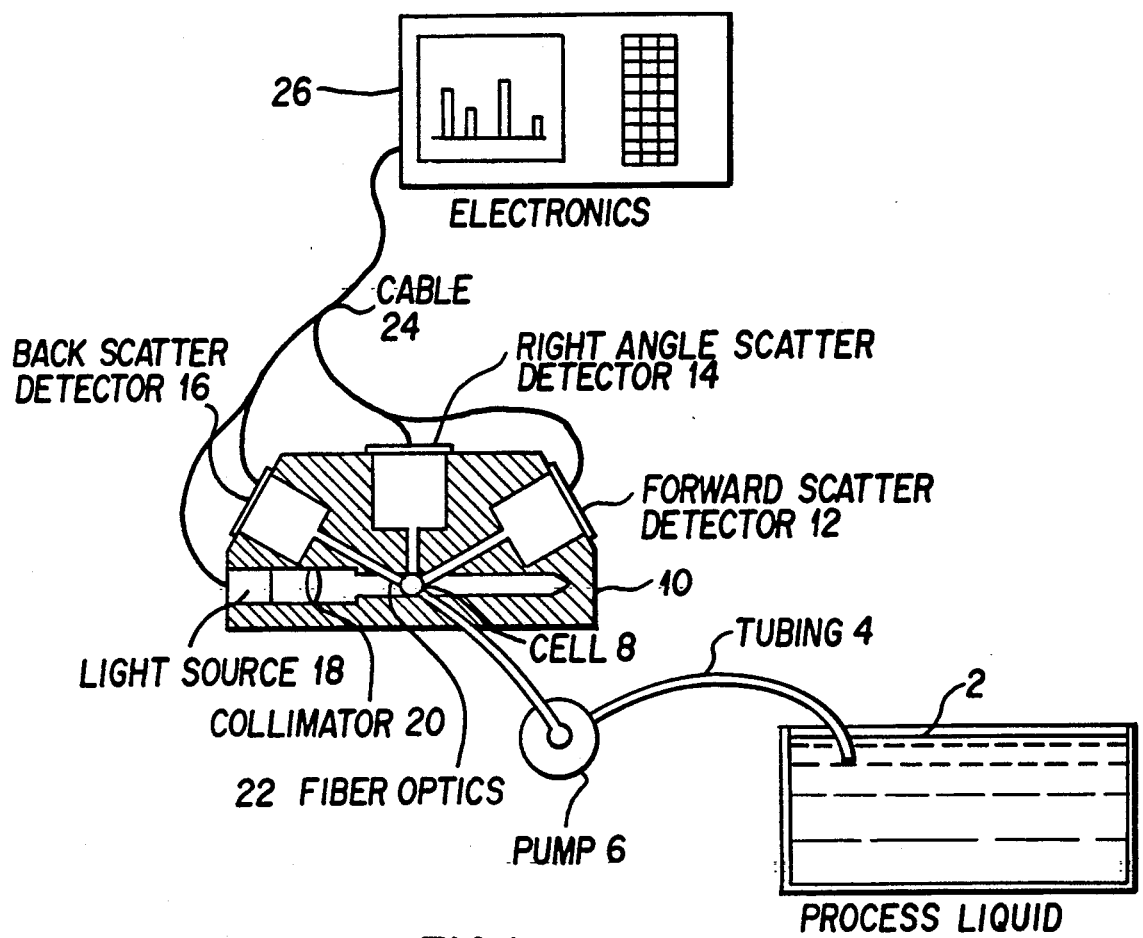
FIG. 1 is a sketch partly in section of a device in accordance with this invention.

FIG. 1 illustrates an embodiment of the present invention in which samples of a liquid process medium 2 are drawn through tubing 4 by pump 6 into cell 8 of a known volume which is located within sensor housing 10. Cell 8 is positioned in close proximity to forward scatter detector 12, right angle scatter detector 14, and back scatter detector 16. The sampling can be either real-time or off-line. Cell 8 is constructed of a material, such as quartz or sapphire, that will not react with the process medium 2 and not contribute particles to the medium.

Cell 8 is illuminated by a light source 18, such as a solid state laser, having a collimator 20 to produce a beam of a known wavelength to impinge upon and illuminate a sampling volume of the liquid process medium 2 and upon any particle or bubble found in the sampling volume of the cell and scatter therefrom.

Within sensor housing 10 fiber optics 22, or alternatively reflectors, collect the scattered light, and separate it into forward, right angle or back scattering, which is detected and converted into electrical signals, proportional to the level of light detected, through detectors 12, 14, and 16 respectively, which detectors may be photo diodes. The electrical signals are transmitted through cable 24 to an electronics module 26.

Electronics module 26 contains conventional circuitry which can process the signals to determine the size and quantity of particles or bubbles or both within process medium 2 based upon the presence or absence of signals consistent with those resulting from back scattering from bubbles.

Figure 2:
FIG. 2 is an illustration of the output of a monitoring device in accordance with this invention.
Figure 2:
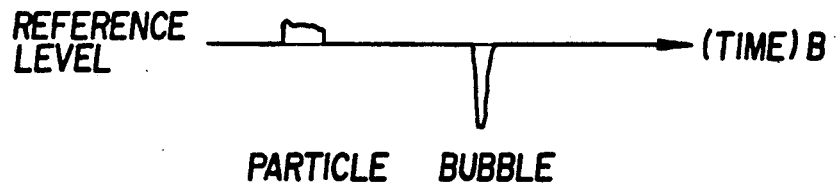

FIG. 2 illustrates the phenomena which makes it possible to distinguish between bubbles and particles. Lines A and B represent the forward/right angle scatter signal and back scatter signal respectively. In the illustration as time passes, first a particle is encountered within the sampling volume. The particle causes a positive impulse to be produced in the forward/right angle scatter signal and a smaller, but still positive, impulse to be produced in the back scatter signal. As time passes a bubble is encountered. The bubble causes a positive impulse to be produced in the forward/right angle signal which is similar to the positive impulse produced by the previous encounter with a particle. However, the bubble causes a relatively narrow bandwidth negative impulse to be produced in the back scatter signal. The recognition of the significance of this negative impulse, which heretofore has been treated as background chatter, is the crux of this invention.

Once the significance of this back scatter produced negative impulse is known, the processed signals can be compared to predetermined limits and used to monitor and control processes in manufacturing, medical or other applications where particle quantity and size are critical.

This invention allows a number of important process factors to be measured:

(a) For a given volume and density of a liquid the change in the signal produced by back scattering can be used to measure the presence and relative size of a bubble.

(b) For a given volume and density of a liquid the change in the signal produced by forward and/or right angle scattering and back scattering can be used to measure the presence and relative size of a particle.

(c) For a given flow rate, a given cell volume, a given sample time, and the number of bubbles within the sample counted, the number of bubbles in a given process medium volume can be statistically determined.

(d) For a given flow rate, a given cell volume, a given sample time, and the number and size of particles counted, the number and size of articles in a given process volume can be statistically inferred, with the inference statistically free from error with regard to interference from bubble detection.

Although this invention has been described with reference to its use in a semiconductor manufacturing process, the ability to discriminate between particles and bubbles within a liquid medium is applicable to any process where such a process control is essential or desirable.

The optical sensor has been described as a laser generated, fiber optics system. However it is within the skill of the art to employ another arrangement using light guides and reflectors or equivalent configurations of optical components.

An enhancement of the process as described which is particularly useful for discriminating between bubbles and particles in the submicron range is the use of ultrasound to generate a localized change in density around a particle. This increasing the sensitivity of the detectors by making particles appear relatively larger as a function of the controlled ultrasonic energy imputed to the sampling volume.

Another embodiment of the principle of this invention is the use of a short wavelength light source for the purpose of stimulating bacteria within a liquid medium to fluoresce. In connection with a system as described herein the use of fluorescence can be used to detect bacteria in the presence of bubbles and particles.

This invention provides a unique method and device for the measurement of particles and bubbles within a liquid medium. Variations and modifications of the embodiments disclosed may be made without departing from the scope of this invention.

We claim:

1. A detecting system for measuring and discriminating between particles and bubbles within a liquid medium comprising:

(a) a source of light for generating a light beam;
    (b) a cell containing a sampling volume to be analyzed and positioned so that said sampling volume is illuminated by said light beam and scatters said light;

(c) sensing means to collect said scattered light and to separate said scattered light into its forward and/or right angle scattering, and back scattering components;

(d) separate detectors positioned to separately receive each scattered light component and to convert each said component to electrical signals proportional to the intensity of the light detected;

(e) signal processing means for determining the size and quantity of particles and bubbles within said sampling volume based upon the unique signature generated by bubbles in the back scatter channel.

2. A device in accordance with claim 1 wherein said light source is a collimated laser diode.

3. A device in accordance with claim 1 wherein said sensing means are fiber optic devices.

4. A device in accordance with claim 1 wherein said sensing means is a lens imaging device.

5. A device in accordance with claim 1 wherein said sensing means is a reflective optical device.

6. A device in accordance with claim 1 wherein said sensing means comprise light pipes which define a collection aperture and transfer the collected light to the respective detectors.

7. A device in accordance with claim 1 in which said particles are enhanced for easier detection by ultrasonic means.

8. A device in accordance with claim 1 for the detection and measurement of bacteria in the presence of particles and bubbles in which said light source is of a wavelength to cause said bacteria to fluoresce.

* * * * *